US00PP34044P2

(12) United States Plant Patent
Booth et al.

(10) Patent No.: US PP34,044 P2
(45) Date of Patent: Mar. 22, 2022

(54) ALMOND TREE NAMED 'BOOTH'

(50) Latin Name: *Prunus dulcis*
Varietal Denomination: Booth

(71) Applicants: The Irene Booth Trust for Richard D. Booth dated November 29, 1999, Orland, CA (US); The Francis and Christine Booth Family Trust dated September 4, 2019, Orland, CA (US)

(72) Inventors: Richard D. Booth, Orland, CA (US); Francis R. Booth, Orland, CA (US)

(73) Assignees: The Irene Booth Trust for Richard D. Booth, Orland, CA (US); The Francis and Christine Booth Family Trust, Orland, CA (US)

( * ) Notice: Subject to any disclaimer, the term of this patent is extended or adjusted under 35 U.S.C. 154(b) by 0 days.

(21) Appl. No.: 17/163,254

(22) Filed: Jan. 29, 2021

(51) Int. Cl.
*A01H 5/08* (2018.01)
*A01H 6/74* (2018.01)

(52) U.S. Cl.
USPC ..... Plt./155
CPC ..... *A01H 6/7427* (2018.05)

(58) Field of Classification Search
USPC ..... Plt./155
CPC ..... A01H 6/7427
See application file for complete search history.

*Primary Examiner* — Anne Marie Grunberg
(74) *Attorney, Agent, or Firm* — Randall Danskin, P.S.

(57) ABSTRACT

A new and distinct variety of almond tree (*Prunus dulcis*) denominated varietally as 'Booth' is described, which produces an attractively light-colored kernel that is mature for harvesting on approximately August 19 to 25 under the ecological conditions prevailing in the San Joaquin Valley of central California.

6 Drawing Sheets

Latin name: *Prunus dulcis*.

Variety denomination: The invention relates to a new, novel, and distinct variety of almond tree, a *Prunus dulcis*, with a variety denomination hereinafter as 'Booth'.

SUMMARY

Origin and Prior Varieties. The present variety of almond tree resulted from a seedling selection (FIG. 2) in an existing 'Nonpareil' (unpatented, self-incompatible variety bred by A. T. Hatch, 1879, Suisun, Calif.) and 'Ne Plus Ultra' (unpatented, self-incompatible variety of French origin, used by A. T. Hatch primarily for pollination) orchard in Orland, Calif. The existing orchard was over 60 years old and the resulting seedling selection was growing on its own rootstock in the middle of a 'Nonpareil' row.

The original seedling 'Booth' (FIG. 1) was discovered as a chance seedling in a 'Nonpareil' and 'Ne Plus Ultra' orchard. It is unclear if 'Nonpareil' was the seed parent or the pollen parent. The nuts of 'Booth' more closely resemble the nuts of 'Nonpareil' than of 'Ne Plus Ultra'. Richard Booth noticed that the leaves of 'Booth' were greener than the rest of the trees in the orchard and the foliage was more dense than 'Nonpareil'. Usually chance seedlings discovered in commercial orchards have bitter nuts, but 'Booth' had large, sweet nuts. A direct graft (FIG. 2) from the original tree (FIG. 1) led to the present variety.

Mr. Booth showed the variety to a nursery with a nut breeding program in 1995. The nursery observed the tree and decided to evaluate nut samples to determine its commercial viability. Nut samples were sent for evaluation and the nuts of 'Booth' were found to be a California-type class of nut with a light cocoa color kernel and good blanch ability with a sweet and consistent kernel taste.

Asexual Reproduction. Asexual reproduction of this new and distinct variety of almond tree was accomplished by budding (bud grafting) the new almond tree onto 'Nemaguard' Rootstock (unpatented). This was performed by the aforementioned nursery, which is located near Oakdale, Calif., beginning in 1995. Subsequent evaluations of succeeding generations of these asexually reproduced plants grown from 1999 to 2005 have shown asexual reproductions run true to the original tree. All characteristics of the original tree, and its fruit, were established and appear to be transmitted through these succeeding asexual propagations.

Comparisons. 'Booth' is a new and distinct variety of almond tree, which is considered of small to medium size, and somewhat less vigorous than 'Nonpareil'. This new tree is also a regular and very productive bearer of relatively large kernels, which have a very smooth pellicle and good eating qualities. This new almond tree has a medium chilling requirement of 450 hours. The 'Booth' almond tree bears fruit which are typically ripe for commercial harvesting and shipment on approximately August 19 to 25 under the ecological conditions prevailing in the San Joaquin Valley of central California. In relative comparison to the 'Nonpareil' almond tree, which is the closest known variety to the variety described herein, the new variety of almond tree bears almonds approximately 10 to 14 days later than 'Nonpareil' that average 1.13 grams per kernel compared to 1.11 grams per kernel for 'Nonpareil'.

BRIEF DESCRIPTION OF THE DRAWINGS

The accompanying drawings are color photographs of the new almond tree 'Booth' under the ecological conditions prevailing in the San Joaquin Valley of central California.

FIG. 3 depicts four (4) whole, shelled almond kernels, seven (7) unshelled almonds, and three (3) unhulled/unshelled almonds. The shelled and displayed almond kernels are exposed in a lateral view, which demonstrates the kernel veining, the relative shape, and the pellicle color. Inner and outer surfaces of partially removed hulls are also shown.

Figure 1:
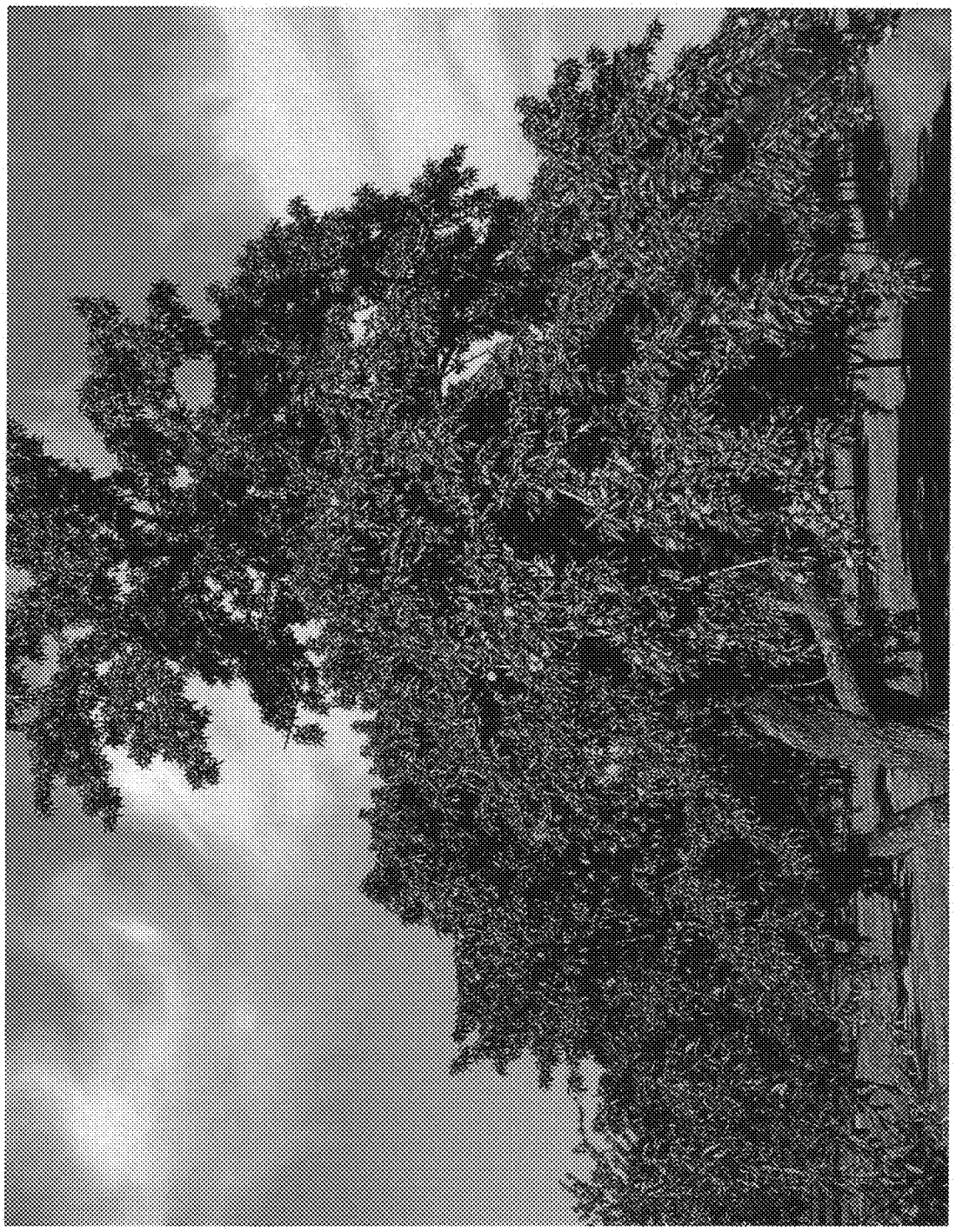
FIG. 1 is a color photograph, which shows the original 'Booth' almond tree (no longer living) in Orland, Calif. This tree was approximately 60+ years old at the time of this photo. This was a chance seedling in a 'Nonpareil' and 'Ne Plus Ultra' orchard.
Figure 2:
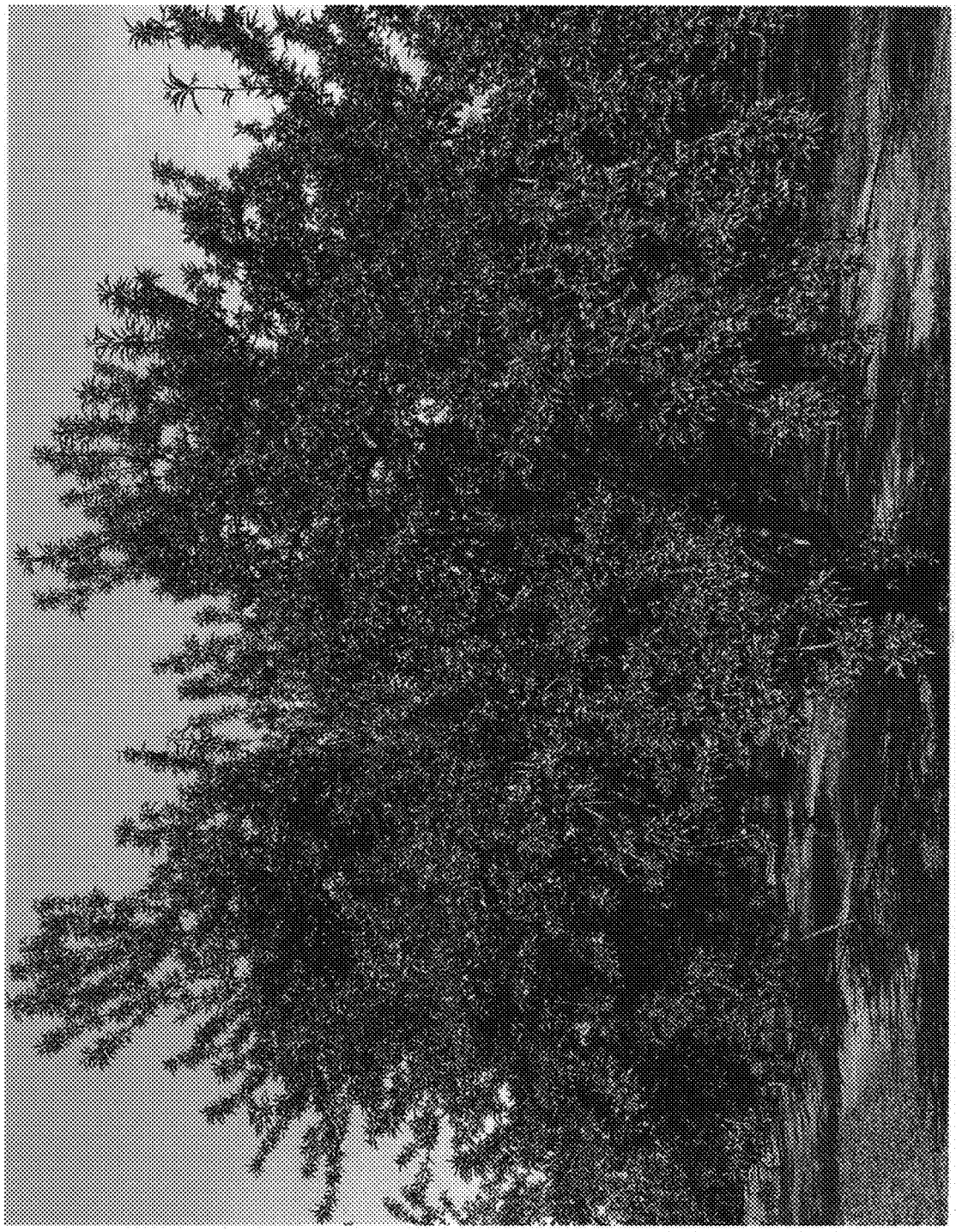
FIG. 2 is a color photograph, which shows a 'Booth' almond tree in Orland, Calif. that was directly grafted from the original mother tree shown in FIG. 1 and is roughly 40+ years old; currently, the oldest living 'Booth' almond tree.
Figure 3:
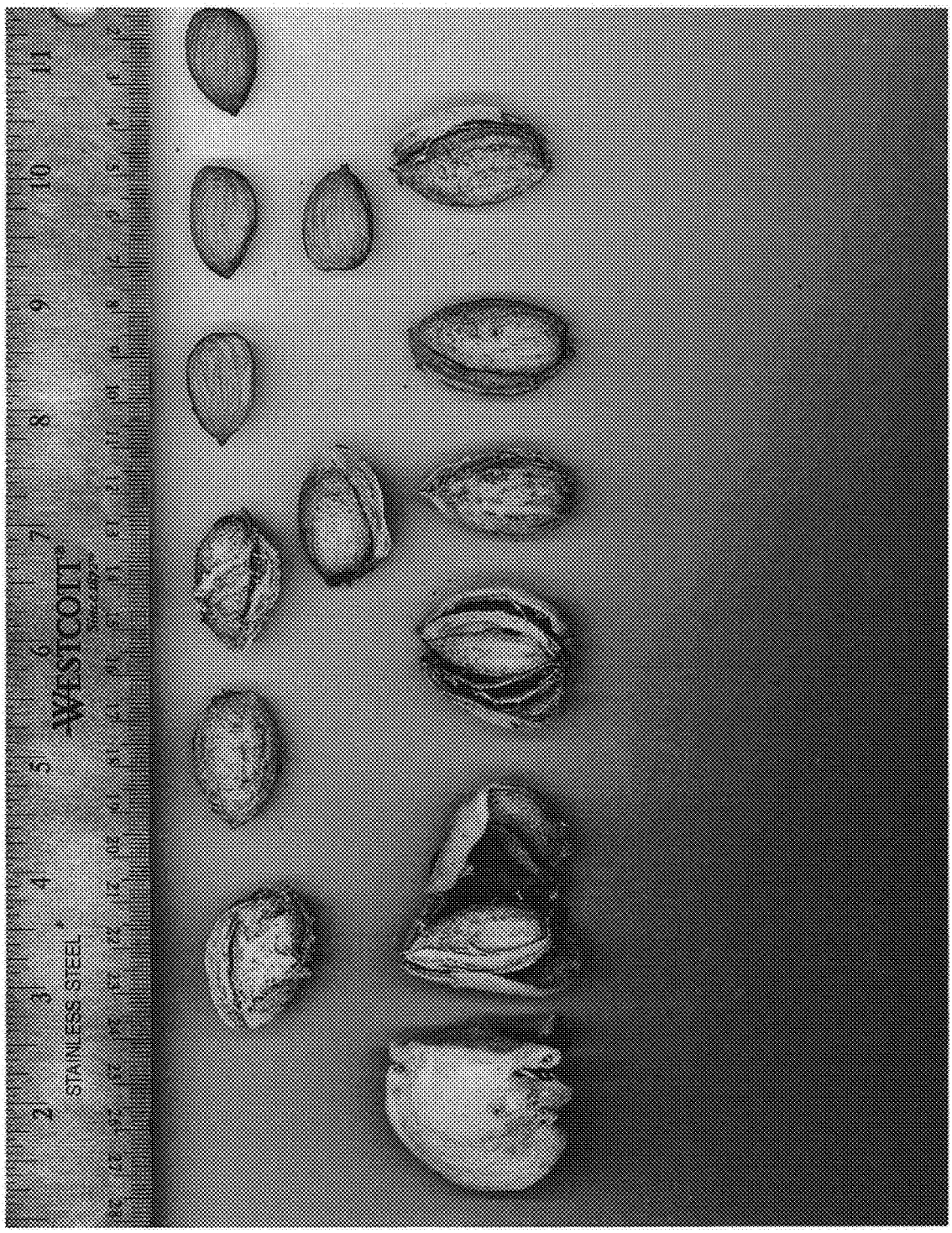
FIG. 3 depicts kernels, shells, and hulls of the new almond tree variety from a tree in Oakdale, Calif. The kernels, shells, and hulls are shown sufficiently matured for harvest.
Figure 4:
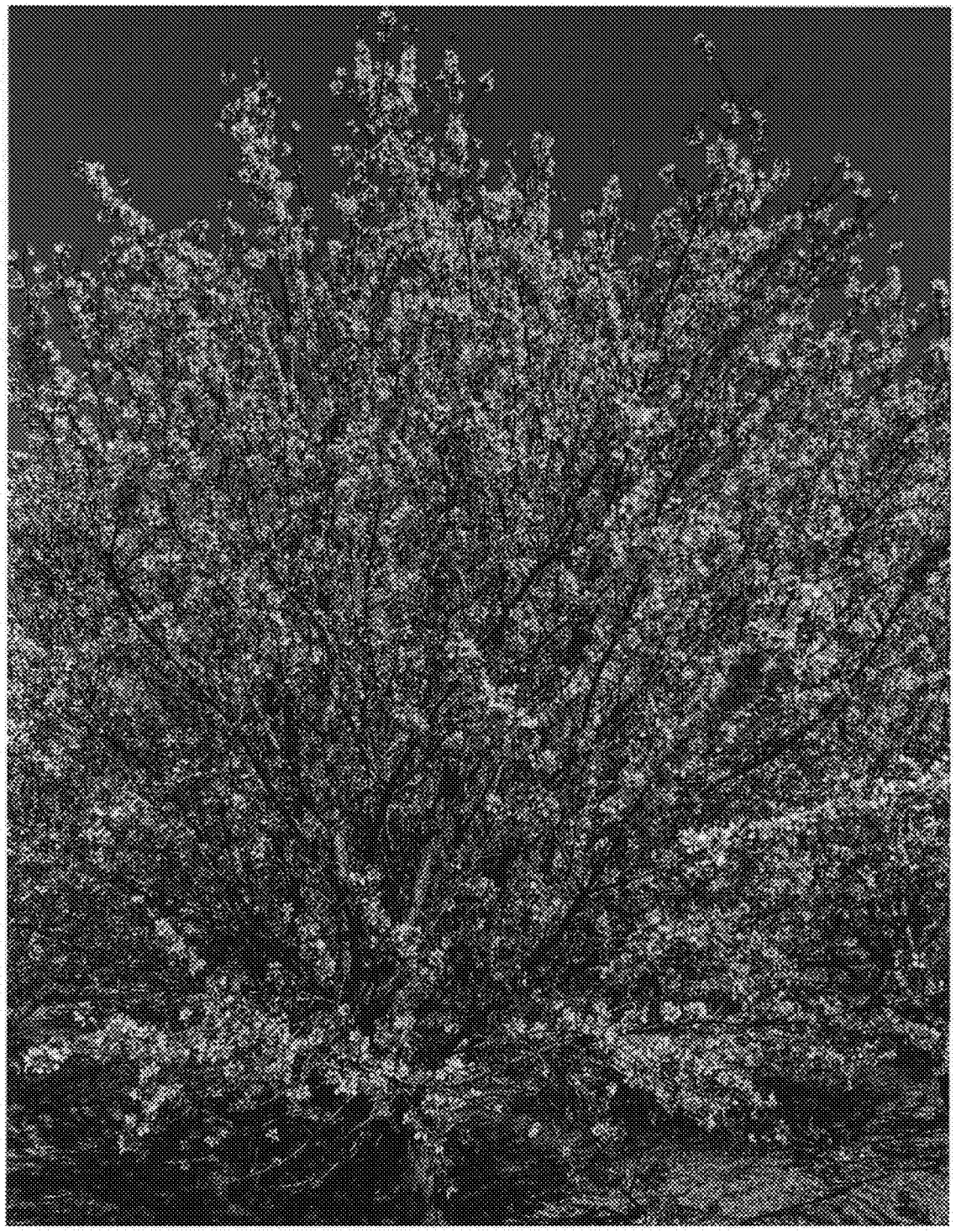
FIG. 4 is a color photograph, which shows a sixth leaf 'Booth' tree in Orland, Calif. in full bloom on 'Nemaguard' root stock.
Figure 5:
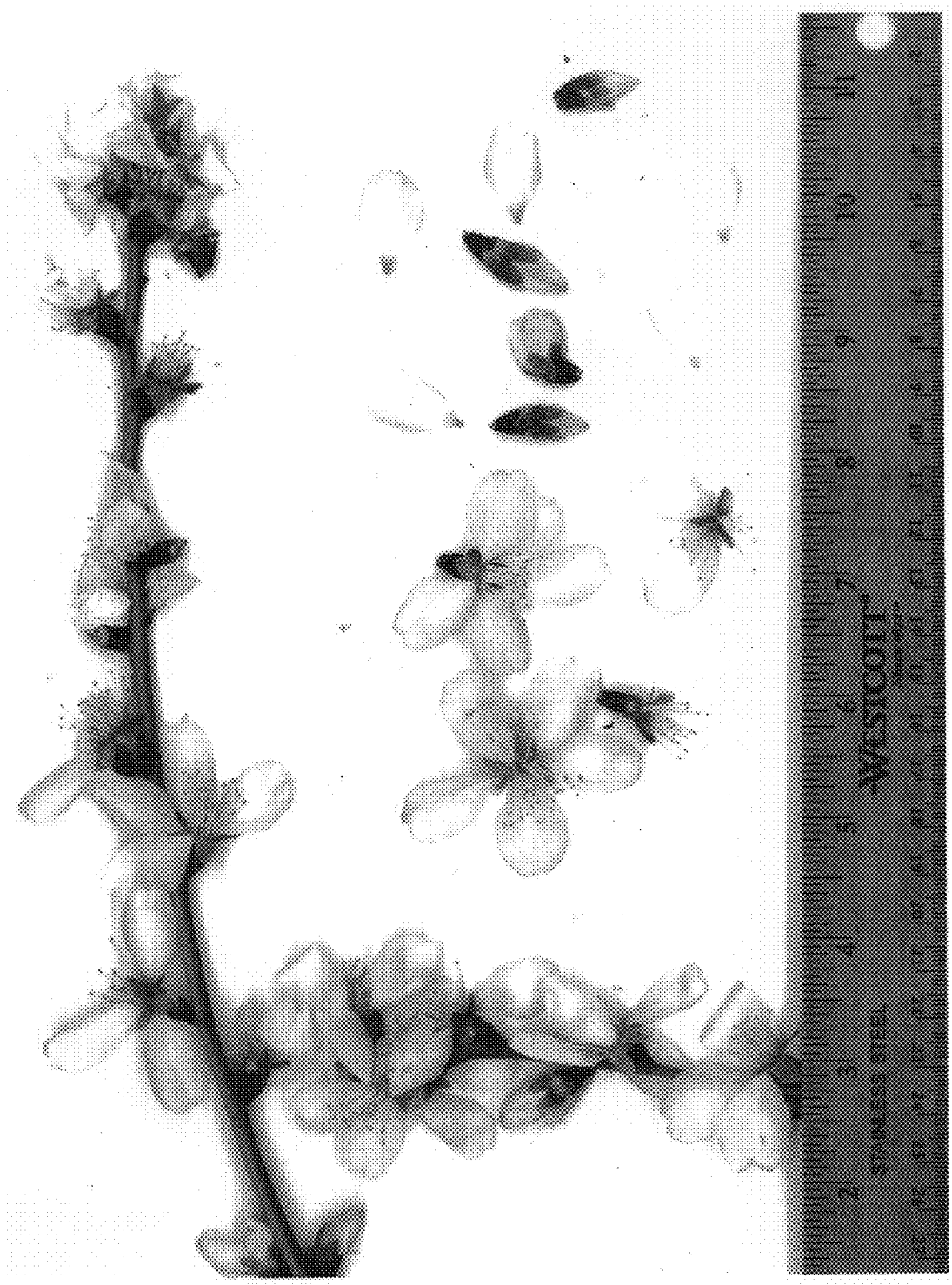
FIG. 5 is a color photograph, which shows a branch with flowers and buds of the 'Booth' variety from a tree in Oakdale, Calif.
Figure 6:
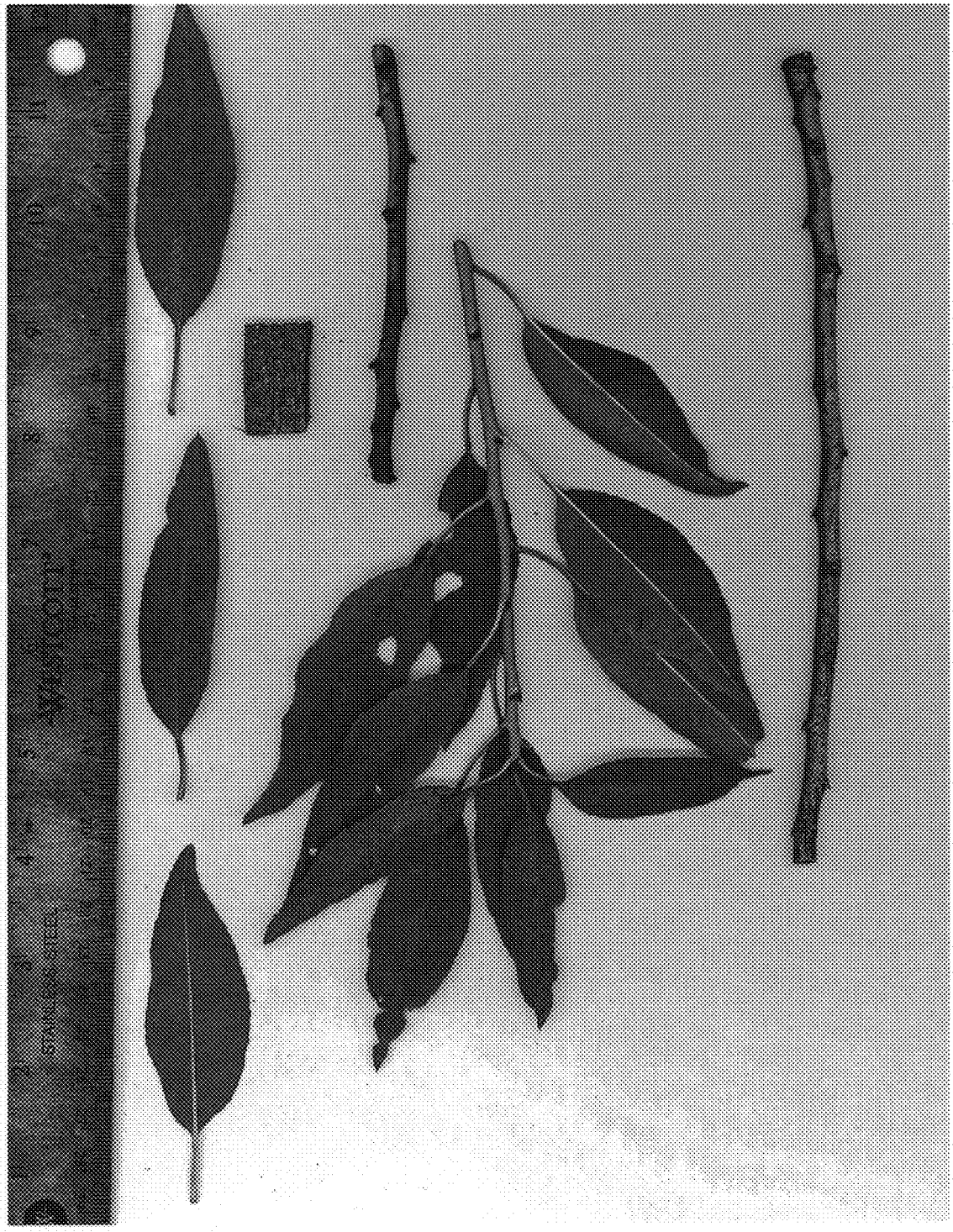
FIG. 6 is a color photograph, which shows the current season's vegetative shoot bearing typical leaves, and three separated leaves showing the dorsal and ventral coloration thereof. A swatch of limb bark and other twigs are shown. Samples were taken from a 'Booth' tree in Oakdale, Calif.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Fourth Edition (2001), hereinafter, "RHS") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of almond tree, the following has been observed during the twelfth fruiting season under the ecological conditions prevailing at orchards located near the town of Fowler, county of Fresno, state of California.

Tree:

*Size.*—Generally considered medium to medium-large and upright in its growth pattern as compared to other common commercial almond cultivars. The tree of the present variety was pruned to a height of approximately 700.0 centimeters (cm) to about 730.0 cm at commercial maturity. Tree pruning, canopy development and ultimate stature of almond orchards are a matter of variety, rootstock, soil potential, cultural inputs and choices. Therefore tree height can be highly variable and therefore not necessarily indicative of the current variety.

*Width.*—Approximately 655.0 cm.

*Vigor.*—Considered moderately vigorous. The present almond tree variety grew from about 200.0 cm to about 210.0 cm in height during the first growing season. The new variety was pruned to a height of approximately 150.0 cm during the first dormant season and primary scaffolds were then selected for the desired tree structure. Tree vigor can be influenced by a number of variables including soil quality, irrigation practices, pruning, and nutrition.

*Productivity.*—Productive. When the new variety is grown in a suitable horticultural zone and under appropriate commercial conditions the current variety can produce volumes of commercial almonds. The number of the fruit set varies with the prevailing climatic conditions and the cultural practices employed and can be increased with inclusion of active bee hives and proximity to compatible foreign pollen sources.

*Bearing.*—Regular. Nut set has been more than adequate during the previous years of observation and, during the past 12 years, on both the original seedling and on subsequent asexually reproduced trees.

*Tree form.*—Upright and typically pruned into a vase shape.

*Density.*—Considered moderately dense. It has been determined that pruning the branches from the center of the tree to obtain a resulting vase shape allows for enhanced air movement and appropriate amounts of sunlight to improve fruit wood development.

*Hardiness.*—The present tree was grown and evaluated in USDA Hardiness Zone 9. The calculated winter chilling requirements of the new tree is approximately 450 hours at a temperature below 7.0° C. The present variety appears to be hardy under typical central San Joaquin Valley climatic conditions.

Trunk:

*Diameter.*—Approximately 28.5 cm in diameter when measured at a distance of approximately 15.24 cm above the soil level. This measurement was taken at the end of the 12th growing season.

*Bark texture.*—Considered moderately rough with numerous folds of papery scarfskin being present. Since bark development and coloration change with advancing tree age, this characteristic varies with the tree vigor, age, and regional conditions.

*Lenticels.*—Flat, oval lenticels are present. The lenticels range in size from approximately 4.0 millimeters (mm) to about 6.0 mm in width, and between about 1.0 and about 2.0 mm in height. The development and size of the trunk lenticels can be influenced, to some degree, by the ambient growing conditions. As trees of this variety mature, lenticels are present, but they are generally covered by increasing layers of cork (mature bark) and, therefore, become less apparent.

*Lenticel color.*—Considered an orange brown (RHS Greyed-Orange Group 163 C).

*Bark coloration.*—Variable, but it is generally considered to be a greyed brown (RHS Greyed-Orange Group 166 A). This bark description was taken from trees in their twelfth leaf which have ruptured the scarf skin with deep furrowing as the trunk expands with age. It should be noted that the coloration of the bark can be influenced by exposure to sunlight and humidity.

Branches:

*Size.*—Considered medium for the variety.

*Diameter.*—Average as compared to other almond varieties. The branches have a diameter of about 22.0 cm when measured during the 12th year after grafting.

*Surface texture.*—Average and furrowing of bark usually occurs by the 4th year of development.

*Crotch angles.*—Primary branches are considered variable and are usually growing at an angle of about 42 to about 56 degrees when measured from a horizontal plane. This characteristic can be influenced, to some degree, by tree vigor, rootstock, time, and severity of pruning and other cultural conditions.

*Current season shoots.*—Surface texture — Substantially glabrous.

*Feather of the shoot.*—Strong.

*Internode length.*—Approximately 15.0 mm to 35.0 mm between nodes. Greater internodal intervals exist nearer the basal end of the shoot and shorter internodal intervals are exhibited nearer the apical shoot tip.

*Color of mature branches.*—Approximately Grey brown (RHS Greyed-Orange Group 166 C).

*Current seasons shoots.*—Color — Medium-light green (RHS Yellow-Green Group 144 C). The color of new shoot tips is considered a bright and shiny green (RHS Yellow-Green Group 145 B). The vegetative shoot color can be significantly influenced by plant nutrition, irrigation practices, and exposure to sunlight.

Leaves:

*Size.*—Considered medium-large for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the amount of ambient light and other cultural factors listed above.

*Length.*—Approximately 85.0 to about 110.0 mm.

*Width.*—Approximately 25.0 to about 29.0 mm.

*Base-shape.*—The leaves generally exhibit equal marginal symmetry relative to the leaf longitudinal axis.

*Form.*—Lanceolate.

*Tip form.*—Acuminate.

*Color.*—Upper Leaf Surface — Dark green (approximately RHS Yellow-Green Group 137 A).

*Color.*—Lower Leaf Surface — Light to medium green (approximately RHS Yellow-Green Group 137 C).

*Texture.*—Glabrous (both sides).

*Venation.*—Pinnately veined.

*Mid-vein.*—Color — Considered a light, yellow-green (approximately RHS Green-White Group 150 C) in the early to mid-period of the growing season.

*Leaf margins.*—Considered entire and smoothly crenate. Occasionally doubly crenate. Form — Considered smooth. Uniformity — Considered generally uniform. Thickness — Considered normal for the species.

*Leaf petioles.*—Form — Considered canaliculated and having a more pronounced trough when viewed from the dorsal aspect. The petiole margin is considered rounded when viewed from the ventral aspect. Size — Considered medium-large for the species. Length — About 20.0 to about 25.0 mm. Diameter — About 1.5 to about 2.0 mm. Color — Light yellow green (approximately RHS Yellow-Green Group 149 C).

*Leaf glands.*—Size — Considered very small for the species; approximately 0.5 mm in length and about 0.5 mm in height. Number — Generally one and less common two glands appear per marginal side are found. Occasionally, glands are only present on one side. More rarely no classifiable glands are present. Type — Glands located at the base of the leaf are predominantly globose in shape.

*Color.*—Considered a medium, light brown approximately (RHS Yellow-Green Group N144 B).

*Leaf stipules.*—Size — Small for this variety. Length — 1.0-2.0 mm. Width — 0.3-0.5 mm. Number — Typically 2 per leaf bud and up to 6 per shoot tip. Form — Lanceolate in form and having a serrated marginal edge. Color — Green (approximately RHS Green Group 139 B) when young, but graduating to a brown color (approximately RHS Greyed-Orange Group 165 A) with advancing senescence. The leaf stipules are generally considered to be early deciduous.

Flower buds:

*Hardiness.*—No winter injury (bud death) has been noted during the years of observation in the central San Joaquin Valley. The new variety of almond tree has not been intentionally subjected to drought, cold or heat stress, and therefore this information is not available.

*Size.*—Variable and dependent on the state of maturity. The flower buds as described were observed approximately 7 days prior to bloom.

*Length.*—Approximately 15.0 mm.

*Diameter.*—Approximately 10.0 mm.

*Distribution.*—Predominantly on spurs.

*Surface texture.*—Pubescent.

*Orientation.*—Considered appressed but appears less so as the blossoms near opening.

*Bud scale color.*—Approximately RHS Greyed-Purple 185 C.

Flowers:

*Date of first bloom.*—Observed on Feb. 12, 2014.

*Blooming time.*—Considered average in relative comparison to other commercial almond cultivars grown in the central San Joaquin Valley. The date of full bloom was observed on Feb. 20, 2014. Approximately 4-5 days before the 'Nonpareil' variety. On average, the time of leaf bud burst occurs 2-3 days after first bloom. The date of full bloom varies slightly with climatic conditions and prevailing cultural practices.

*Duration of bloom.*—Approximately 8 days. Occasionally 10 days or slightly more. This particular characteristic varies slightly with the prevailing climatic conditions.

*Class.*—Considered a perfect flower, complete and perigynous.

*Type.*—The variety is considered to have a showy type flower. Petals are largely unappressed relative to the vertical axis of the flower.

*Size.*—Considered medium large for the species. The flower diameter at full bloom is approximately 41.0 to 46.0 mm.

*Bloom quantity.*—Considered abundant (14 average flowers per 25 cm length of branch).

*Bud frequency.*—Generally two flower buds appear per node; occasionally, one flower bud per node is observed. Larger numbers of flower buds are present on mature complex spurs.

*Petal size.*—Generally considered medium for the species. Petal Length — Approximately 17.0 to 20.0 mm. Petal Width — Approximately 13.0 to 15.0 mm.

*Petal form.*—Considered broadly ovate.

*Petal count.*—Nearly always 5.

*Petal texture.*—Glabrous (both sides).

*Petal color.*—Considered a light pink at the popcorn stage (RHS Red Group 56A) and becomes lighter during enfloration to nearly a pure white (RHS White Group N155 D).

*Fragrance.*—Slight (honey-like smell).

*Petal claw.*—Form — The claw is considered obovatus and is generally medium-small and more elongated. Length — Approximately 15.0 to 16.0 mm. Width — Approximately 7.5 to 9.0 mm.

*Petal margins.*—Generally considered variable from nearly smooth to moderately undulate.

*Petal apex.*—Often the petal margin exhibits a shallow and wide recess at tip. Width — Approximately 2.0 mm. Depth — 2.0 mm.

*Flower pedicel.*—Length — Considered medium-long with an approximate length of about 3.5 to about 4.5 mm. Diameter — Approximately 2.5 mm. Color — A medium brown, approximately (RHS Grey-Brown Group 199 C), depending on pedicel and fruit maturity and timing of visual observance. Surface — Glabrous.

*Floral nectaries.*—Color — Considered a deep reddish orange (approximately RHS Greyed-Red Group 178 D).

*Calyx.*—Surface Texture — Generally glabrous. Color — A dull red (approximately RHS Greyed-Red Group 178 C).

*Sepals.*—Surface Texture — The surface has a short, fine pubescent texture. Number — 5 sepals. Size — Average and ovate in form. Sepal Length — Approximately 4.0 to 6.0 mm. Sepal Width — Approximately 3.5 to 4.5 mm. Sepal Shape — Generally obovate. Sepal Margin — Considered smooth and entire. Sepal Color — A dull greenish brown (approximately RHS Yellow-Green Group 152 C).

*Anthers.*—Generally — Average in size (15 mm) with the stigma below the anthers. Color — Red to yellow-gold when viewed dorsally at dehiscence (approximately RHS Yellow Group 13 B).

*Pollen production.*—Pollen is abundant and has a yellow color (approximately RHS Yellow Group 13 C).

*Fertility.*—Self-incompatible.

*Filaments.*—Size — Approximately 9.0 to 11.0 mm in length. Approximately 0.5 to 0.75 mm in width. Color — Considered white to a bright white (RHS White Group 155 C).

*Pistil.*—Number — Nearly always one. Generally — Medium small in length. Length — Approximately 11.0 to about 13.5 mm in length including the ovary. Color — Considered a very pale yellow-green (approximately RHS Greyed Yellow Group 160 C). Surface Texture — The variety has a pubescent pistil.

Nut crop:

*Productivity.*—Productive. Variety is very precocious.

*Maturity when described.*—Ripe for commercial harvest condition.

*Date of first harvest.*—Approximately 10 to 14 days after the 'Nonpareil' variety, approximately August 19 to 25. The date of harvest can vary slightly with the prevailing climatic conditions, crop load, rootstock, and the current cultural practices.

*Distribution.*—Almonds are generally well clustered on bearing spurs spread evenly throughout the bearing canopy.

*Tenacity.*—Shell adhesion is firm until harvest. Nut removal is thorough at harvest.

Hull:

*Surface.*—Relatively smooth prior to and after harvest. Hull is covered with short fine pubescence.

*Form.*—Elliptical.

*Thickness.*—Considered thin at time of kernel maturity. Very little mesocarp pulp or fibers adhere to the shell.

*Flesh.*—Leathery, becoming brittle when dry.

*Suture.*—Considered smooth.

*Color.*—A dull tan color (approximately RHS Greyed-Orange Group 165 D).

*Typical weight.*—Approximately 3 to 5 grams. This characteristic is quite dependent upon the prevailing cultural practices.

*Dehiscence.*—Open and widely flaring with clean separation at the suture and throughout the mesocarp.

*Adherence.*—Very weak and easily removed in the hulling process.

Kernel:

*Maturity when described.*—Firm, dry pellicle condition, approximately Aug. 22, 2019. The date of harvest can vary with the prevailing climatic conditions, crop loads, and cultural practices.

*Size.*—Generally — Considered large and very uniform.

*Average length.*—Approximately 23.0 to about 25.0 mm.

*Average width.*—Approximately 13.0 to about 15.0 mm.

*Average thickness.*—Approximately 7.0 to about 10.0 mm. These dimensional characteristics are quite dependent upon crop load and the prevailing cultural practices.

*Form.*—Generally, the kernels are very uniform in shape. Compared to 'Sonora' variety (unpatented), the kernels of the present variety are slightly broader and slightly darker.

*Color.*—Considered a light golden brown (RHS Greyed-Orange 164 C).

*Kernel shape.*—Apex — Shape — Rounded to slightly retuse. Base — Shape — Slightly oblique relative to the vertical axis.

*Pellicle.*—Thickness — Considered medium in thickness and tenacious to the flesh. Surface Texture — Short, fine, tight pubescence. Surface veining is present throughout the pellicle. Color of veins — Considered a medium brown, approximately (RHS Greyed-Orange 166 C).

*Taste.*—Mild, pleasant, non-astringent.

*Weight.*—Approximately 1.35 grams/kernel, although the weight of kernels can be highly affected by climatic conditions and cultural practices. It is possible to observe kernels with higher and lower weight.

*Texture.*—Firm and dense.

*Aroma.*—Not apparent.

*Eating Quality.*—Considered very good.

Shell:

*Type.*—Considered a freestone.

*Size.*—It is generally considered to be medium for the species. The shell size varies significantly depending upon the tree vigor, the crop load, and the prevailing growing and cultural conditions under which the tree was grown.

*Length.*—Average, about 30.0 to about 35.0 mm.

*Width.*—Average, about 22.0 to about 25.0 mm.

*Thickness.*—Average, about 12.0 to about 16.0 mm.

*Form.*—Roughly ovoid.

*Base.*—Shape — The stone is considered shortly attenuate.

*Apex.*—Shape — The shell exhibits a slight to prominently cuspidate apex.

*Shell surface.*—Surface Texture — Considered reasonably smooth with considerable pitting with almost nonexistent furrowing or ridging. Ventral Edge — The ventral edge generally exhibits a thin, fine, and protruding fin at the sutural margin. Dorsal Edge — Shape — Generally considered even. The folds of the surface ridges appearing on the external margins often end gently along the suture.

*Color.*—The color of a mature, dry stone is generally considered a dull brown, approximately (RHS Greyed-Orange Group 164 B).

*Use.*—The present variety 'Booth' is considered to be an almond tree of the early mid-season of maturity and produces kernels that are useful in various almond categories and are blanchable.

*Keeping quality.*—Appears excellent.

*Resistance to insects and disease.*—No particular susceptibilities were noted. The present variety has not been intentionally tested to expose or detect any susceptibilities or resistances to any known plant, fruit diseases, insect, frost, winter injury or other environmental factors.

Although the new variety of almond tree possesses the described characteristics when grown under the ecological conditions prevailing near Fowler, Calif., in the central part of the San Joaquin Valley of California, it should be understood that variations are to be expected in the usual magnitude and characteristics incident to changes in growing conditions, fertilization, pruning, pest control, frost, climatic variables, and horticultural management.

Having thus described and illustrated a new variety of almond tree, what is claimed to secure a plant letters patent is:

1. A new distinct variety of almond tree, substantially as illustrated and described, which is characterized principally as to novelty by producing an attractively light-colored kernel that is mature for harvesting on approximately August 19 to 25 under the ecological conditions prevailing in the San Joaquin Valley of central California.

* * * * *